(12) United States Patent
Seyedsayamdost

(10) Patent No.: US 10,941,434 B2
(45) Date of Patent: Mar. 9, 2021

(54) METHOD FOR AWAKENING SILENT GENE CLUSTERS IN BACTERIA AND DISCOVERY OF CRYPTIC METABOLITES

(71) Applicant: The Trustees of Princeton University, Princeton, NJ (US)

(72) Inventor: Mohammad R. Seyedsayamdost, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 190 days.

(21) Appl. No.: 16/104,319

(22) Filed: Aug. 17, 2018

(65) Prior Publication Data

US 2018/0355397 A1 Dec. 13, 2018

Related U.S. Application Data

(62) Division of application No. 15/124,869, filed as application No. PCT/US2015/019696 on Mar. 10, 2015, now Pat. No. 10,077,460.

(60) Provisional application No. 61/950,291, filed on Mar. 10, 2014.

(51) Int. Cl.
| | | |
|---|---|---|
| C40B 30/06 | (2006.01) |
| C12Q 1/02 | (2006.01) |
| C12N 15/52 | (2006.01) |
| C12P 17/06 | (2006.01) |

(52) U.S. Cl.
CPC ............ C12Q 1/025 (2013.01); C12N 15/52 (2013.01); C12P 17/06 (2013.01)

(58) Field of Classification Search
USPC ........................................................ 506/10
See application file for complete search history.

(56) References Cited

U.S. PATENT DOCUMENTS 7,026,460 B2   4/2006  Roberts et al.
8,222,434 B1   7/2012  Greenberg et al.

FOREIGN PATENT DOCUMENTS

WO       2013171158 A1    11/2013

OTHER PUBLICATIONS

Chandler et al. mbio.asm.org vol. 3, No. 6 Nov./Dec. 2012. (Year: 2012).*
Seyedsayamdost et al. Org. Lett. 2010, 12, 4, 716-719 (Year: 2010).*
International Search Report for PCT/US2015/019696, dated Jul. 10, 2015.
Written Opinion for PCT/US2015/019696, dated Jul. 10, 2015.
Walsh C (2003) "Where will new antibiotics come from?" Nat Rev Microbiol 1: 65-70.
Nathan C (2004) "Antibiotics at the crossroads." Nature 431: 899-901.
Newman DJ, Cragg GM (2012) "Natural products as sources of new drugs over the 30 years from 1981 to 2010." J Nat Prod 75: 311-335.
Newman DJ, Cragg, GM, Snader KM (2000) "The influence of natural products upon drug discovery." Nat Prod Rep 17: 215-234.
Clatworthy AE, Pierson E, Hung DT (2007) "Targeting virulence: a new paradigm for antimicrobial therapy." Nat Chemn Biol. 3: 541-548.
Falagas ME, et al. (2005) "Outcome of infections due to pandrug-resistant (PDR) Gram-negative bacteria." BMC Infect Dis 5: 24-30.
Klevens RM, et al. (2007) "Invasive methicillin-resistant *Staphylococcus aureus* infections in the United States." JAMA 298: 1763-1771.
Fischbach MA, Walsh CT (2009) "Antibiotics for emerging pathogens" Science 325: 1089-1093.
Clardy J, Fischbach MA, Walsh CT (2006) "New antibiotics from bacterial natural products." Nat Biotechnol 24: 1541-1551.
Baltz RH (2008) "Renaissance in antibacterial discovery from actinomycetes." Curr Opin Pharmacol 8:557-563.
Nett M, Ikeda H, Moore BS (2009) "Genomic basis for natural product biosynthetic diversity in the actinomycetes." Nat Prod Rep 26: 1362-1384.
Bentley SD, et al. (2002) "Complete genome sequence of the model actinomycete Streptomyces coelicolor A3(2)." Nature 417: 141-147.
Oliynyk M, et al. (2007) "Complete genome sequence of the erythromycin-producing bacterium *Saccharopolyspora erythraea* NRRL23338." Nat Biotechnol 25: 447-453.
Zerikly M, Challis GL (2009) "Strategies for the discovery of new natural products by genome mining." Chembiochem 10: 625-633.
Blin K, et al. (2013) "antiSMASH 2.0—a versatile platform for genome mining of secondary metabolite producers." Nucleic Acids Res 41: W204-W212.
Shank EA, Kolter R (2009) "New developments in microbial interspecies signaling." Curr Opin Microbiol 12: 205-214.
Seyedsayamdost MR, Traxler MF, Clardy J, Kolter R (2012) "Old meets new: using interspecies interactions to detect secondary metabolite production in actinomycetes." Methods Enzymol 517: 89-109.
Galyov EE, Brett PJ, DeShazer D (2010) "Molecular insights into Burkho/deria pseudomallei and Burkholderia mallei pathogenesis." Annu Rev Microbiol 64: 495-517.

(Continued)

Primary Examiner — Jana A Hines
Assistant Examiner — Khatol S Shahnan Shah
(74) Attorney, Agent, or Firm — Meagher Emanuel Laks Goldberg & Liao, LLP.

(57) ABSTRACT

The majority of clinically used antibiotics and anticancer agents are derived from bacterial small molecules. These molecules are produced by dedicated biosynthetic gene clusters, sets of genes that are responsible for the step-wise generation of the target small molecule. Recent investigations have indicated, to the surprise of many experts, that the majority of these biosynthetic genes are inactive or 'silent' for unknown reasons. Thus under typical bacterial culturing conditions, these genes are not expressed and consequently the bioactive small molecule products are not synthesized. Disclosed is a method for high throughput screening of elicitors of cryptic metabolites, a method for producing cryptic metabolites, and a new family of cryptic metabolites, the acybolins, as well as their complete structural elucidation.

4 Claims, No Drawings

(56) References Cited

OTHER PUBLICATIONS

Biggins JB, Ternei MA, Brady SF (2012) "Malleilactone, a polyketide synthase-derived virulence factor encoded by the cryptic secondary metabolome of Burkholderia pseudomallei group pathogens." J Am Chem Soc 134: 13192-13195.

Franke J, Ishida K, Hertweck C (2012) "Genomics-driven discovery of burkholderic acid, a noncanonical cryptic polyketide from human pathogenic *Burkholderia* species." Angew Chem Int Ed 51: 11611-11615.

Gallagher LA, et al. (2013) "Sequence-defined transposon mutant library of Burkholderia thailandensis." MBio 4: 00604-00613.

Duerkop BA et al. (2009) "Quorum-sensing control of antibiotic synthesis in Burkholderia thailandensis." J Bacteriol 191: 3909-3918.

Seyedsayamdost MR et al. (2010) "Quorum-sensing-regulated bactobolin production by Burkholderia thailandensis." Org Lett 12: 716-719.

Biggins JB, Gleber CD, Brady SF (2011) "Acyldepsipeptide HDAC inhibitor production induced in Burkholderia thailandensis." Org Lett 13:1536-1539.

Nguyen T, et al. (2008) "Exploiting the mosaic structure of trans-acyltransferase polyketide synthases for natural product discovery and pathway dissection." Nat Biotechnol 26: 225-233.

Ishida K, Lincke T, Hertweck C (2012) "Assembly and absolute configuration of short-lived polyketides from Burkholderia thailandensis." Angew Chem Int Ed Engl 51: 5470-5474.

Vial L et al. (2008) "Burkholderia pseudomallei, B. thailandensis, and B. ambifaria produce 4-hydroxy-2-alkylquinoline analogues with a methyl group at the 3 position that is required for quorum-sensing regulation." J Bacteriol 190: 5339-5352.

Barrett AR et al. (2008) "Genetic tools or allelic replacement in *Burkholderia* species." Appl Environ Microbiol 74: 4498-4508.

Davies J (2006) "Are antibiotics naturally antibiotics." J Ind Microbiol Biotechnol 33: 496-499.

Yim G, Wang HH, Davies J (2007) "Antibiotics as signaling molecules." Philos Trans R Soc Lond B Biol Sci 362: 1195-1200.

Patankar AV, Gonzalez JE (2009) "Orphan LuxR regulators of quorum sensing." FEMS Microbiol Rev 33: 739-756.

Yoon V, Nodwell JR (2013) "Activating secondary metabolism with stress and chemicals." J Ind Microbiol Biotechnol, in press. PMID: 24326978.

Traxler MF, Watrous JD, Alexandrov T, Dorrestein PC, Kolter R (2013) Interspecies interactions stimulate diversification of the Streptomyces coelicolor secreted metabolome. MBio 4: 00459-00513.

* cited by examiner

METHOD FOR AWAKENING SILENT GENE CLUSTERS IN BACTERIA AND DISCOVERY OF CRYPTIC METABOLITES

CROSS-REFERENCE TO PRIOR FILED APPLICATIONS

This application claims priority to U.S. provisional application Ser. No. 15/124,869 (now U.S. Pat. No. 10,077,460), which was filed on Sep. 9, 2016, which is the National Stage Entry of PCT/US2015/019696, filed on Mar. 10, 2015, which are incorporated herein in their entirety by reference. This application also claims priority to U.S. Provisional Application 61/950,291, which was filed Mar. 10, 2014, which is incorporated in its entirety herein by reference.

BACKGROUND OF THE INVENTION

Recent genome sequencing efforts, which have revealed that our current discovery methods access, at best, 10% of the small molecule repertoire of bacteria. A detailed analysis of the sequenced genomes of actinomycetes, the group of bacteria responsible for over 50% of all antibiotics, has demonstrated that the great majority of biosynthetic gene clusters, the sets of genes responsible for production of bioactive compounds, remain inactive or 'silent' for unknown reasons. Given the track record of natural products as therapeutics, these clusters, dubbed silent or cryptic gene clusters, harbor an extensive supply of potential drug candidates, and successful approaches that systematically awaken them would have a profound impact on drug discovery.

The problem of silent gene clusters is challenging because an unknown signal activates an uncharacterized gene cluster leading to the production of a new metabolite. There are three variables in this process, two of which can be determined experimentally or computationally: bioinformatic methods allow for facile identification of genes that generate nonribosomal peptides, polyketides, and terpenes, and pinpointing gene assemblies of novel metabolites within these families can be performed with good fidelity. Once activated, the product of the gene cluster can be experimentally identified by differential metabolomics facilitating its isolation and structural elucidation via multi-dimensional NMR. Thus, the problem of crypticity may be reduced to the large variety of signals that may act as elicitors or activators of silent clusters.

Thus far, no method has been described that allows for identification of elicitors of a given silent gene cluster. An efficient platform that enables discovery of small molecule activators would allow scrutiny of the regulatory pathways that lead to induction of silent biosynthetic clusters as well as structural and functional elucidation of their products.

BRIEF SUMMARY OF THE INVENTION

A method for high-throughput screening to aid in discovering an agent able to activate silent bacterial gene clusters is disclosed. The method includes providing bacterial cells, which may be of a species existing naturally in soil or other environments, containing at least one gene cluster that is silent or lowly-expressed. Then, genetically modifying the gene cluster to include at least one reporter gene within the gene cluster. The reporter gene inserted into the gene cluster may include, but is not limited to, green fluorescent protein (GFP) or other fluorescent proteins (such as CFP, YPF, or RFP), the lux operon, and β-galactosidase (lacZ). One bacterial cell, group of cells, or cell culture is used as a control; at least one other cell, group, or culture is used as a test group. The test group is exposed to different stress conditions, including exposure to a test compound or a library of small molecules, of synthetic, semi-synthetic or natural origins. The expression of at least one of reporter gene is then measured for each group of bacterial cells, groups of cells, or cell cultures. An elicitor of a gene cluster has been identified when the expression of the reporter gene in the test group is a statistically significant amount greater than is expressed by the control group.

The method may also include identifying a molecule that results from the activation of said gene clusters. One type of molecule that could result is a cryptic metabolite.

A kit for discovering an agent which is able to activate silent bacterial gene clusters is also disclosed. The kit includes a bacteria configured with a reporter gene located within a silent or lowly-expressed gene cluster in the bacteria. The reporter gene inserted into the gene cluster may include, but is not limited to, green fluorescent protein (GFP), the lux operon, and β-galactosidase (lacZ).

A method for producing cryptic metabolites is also disclosed. The method includes providing a bacterial cell containing at least one gene cluster, that is silent or lowly-expressed, then exposing the bacterial cell to a small molecule modulator or small molecule modulator library. The small molecule modulator library may consist of functionally and structurally diverse molecules, any of which may include, but are not limited to, an antibiotic.

A cryptic metabolite resulting from the above method is also disclosed. The metabolite is a molecule having a formula:

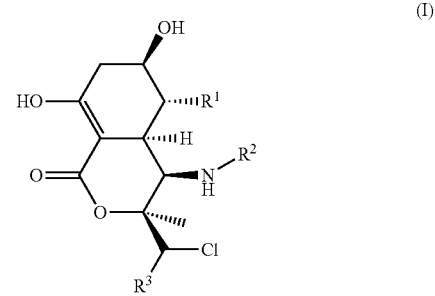

(I)

wherein $R^1$ consists of H or OH, $R^2$ comprises a plurality of amino acids and at least one functional group, and $R^3$ consists of H or Cl. The plurality of amino acids utilized may include, but are not limited to, alanine, glycine, or both. Additionally, the functional group may include an acyl group, which may comprise a carbon chain having between about 2 to about 20 carbons in length, or preferably between about 6 to about 12 carbons in length.

DETAILED DESCRIPTION OF THE INVENTION

The present disclosure generally relates to cryptic metabolites and awakening silent gene clusters in bacteria. Specifically, it discloses a method for screening of elicitors or activators of silent gene clusters in bacteria, a kit to enable such screenings, a method for activating silent gene clusters, and a cryptic metabolite resulting from such activation.

The disclosed screening method begins with acquiring bacteria having at least one silent or lowly-expressed gene cluster. The bacteria are then genetically modified to include a reporter gene within the silent or lowly-expressed gene cluster. One quantity of bacteria is used as a control group, and at least one other quantity of bacteria is used as one or more test groups. The test group or groups are exposed to at least one test compound. While only one test compound may be tested, and thus, only one test group is required, this method allows for any number of test compounds to be tested. Additionally, any class of compound may be tested, which include but are not limited to, vitamins, muscle relaxants, general agonists, estrogens, antifungals, lipid biosynthesis inhibitors, and antibacterials. The expression of the reporter genes are measured in the control group and each test group. A test compound will be considered an elicitor or an activator if the measured expression of the test group is a statistically significant amount greater than that of the control group.

In one example of the high throughput screening method, the silent malleilactone (mal) cluster in Burkholderia thailandensis E264 (hereafter E264), was targeted. To monitor expression of this cluster, a translational lacZ fusion to malL, a gene essential for the biosynthesis of malleilactone, was utilized (hereafter malL-lacZ). MalL-lacZ is not expressed under standard growth conditions and served as a negative control. A lacZ reporter in btaK, which is quorum sensing-regulated and expressed at high cell densities, provided a positive control.

Bacterial growth was carried out in lysogeny broth (LB) supplemented with 50 mM Mops, pH 7.0 (hereafter, LB-Mops). The pH was adjusted with a 5-6 N NaOH solution. To commence the screen, malL-lacZ from an LB agar plate was used to inoculate 5 mL of LB-Mops in a sterile 14 mL bacterial culture tube. The culture was grown overnight at 30° C. and 250 rpm. After 12-16 h, its $OD_{600\,nm}$ was determined on an Ultraspec 5300 Pro Spectrophotometer (Amersham Biosciences). The culture was diluted into 100 mL of LB-Mops to give a final $OD_{600\,nm}$ of 0.05. Subsequently a volume of 45 µL was dispensed into each of four sterile, white 384-well plates (Corning) using a WellMate automated dispenser (Matrix Technologies) at the ICCB-L. Using a Compound Transfer Robot (Seiko) equipped with a calibrated stainless steel pin transfer tool (V&P Scientific), each well was supplemented with 0.1 µL of the at least one compound from a 640-member-containing library. The compounds were dispensed into columns 3 through 22 on each plate, while columns 1 and 2 contained the negative control (malL-lacZ in the absence of any library compounds) and columns 23 and 24 contained the positive control (btaK-lacZ). Between each dispense cycle, the transfer tool pins were washed in MeOH, sonicated in a MeOH/water mixture, and dried with pressurized air. Each plate was covered with a Breathe-Easy sealing membrane (Sigma), vortexed briefly on a plate vortexer, and cultured at 30° C. and 230 rpm for 12 h in a Multitron Shaker (ATR) equipped with a green sealing tray. To maintain constant humidity, several 1 L Erlenmeyer flasks containing 200 mL of water were also placed inside the shaker. After 12 h, the plates were removed from the shaker and rested at room temperature for 5 minutes. The β-Glo reagent (Promega) was used to monitor lacZ activity. The reagent was diluted 2:1 with water. Then, each well was supplemented with 30 µL of the diluted β-Glo reagent using the WellMate automated dispenser, and subsequently vortexed, and incubated in the dark at room temperature for 45 minutes. Total end-point luminescence was then determined on an EnVision Multilabel Reader (PerkinElmer). The optimization wizard in the EnVision software was used to optimize plate dimensions and minimize cross-talk yielding a software-derived correction factor of 0.27. The Z'-score was calculated according to equation 1, where $\sigma_p$ and $\sigma_n$ correspond to the standard deviation of the positive (btaK-lacZ) and negative (malL-lacZ in the absence of elicitors) controls, respectively, while $\mu_p$ and $\mu_n$ correspond to the mean lacZ activity for the positive and negative controls. Standard Z-scores for each compound in the library in the actual screen were calculated using equation 2, where $\mu_c$ corresponds to the mean lacZ activity for each compound in the library, $\mu_n$ corresponds to the mean of the negative control on the same assay plate (columns 1 and 2), and $\sigma_n$ corresponds to the standard deviation of the negative control.

$$Z' = 1 - \left( \frac{3(\sigma_p + \sigma_n)}{\mu_p - \mu_n} \right) \qquad (1)$$

$$Z = \left( \frac{\mu_p - \mu_n}{\sigma_n} \right) \qquad (2)$$

This method provided an optimized, robust screening assay with a Z' value of 0.51 in a 384-well format. A total of nine potential elicitors having Z-scores between 6 and 21 were observed.

It should be understood by a practitioner that while lacZ was utilized in this example, any appropriate reporter gene, or combination or reporter genes would produce similar results. This includes, without limitation, green fluorescent proteins (GFP), red fluorescent proteins (RFP), β-Galactosidase (GUS), and luciferase. It also includes combinations of reporter genes within the same strain.

Once the above screening has occurred, identification of molecules may occur, utilizing standard analytical techniques, including but not limited to RT-qPCR, GC, HPLC, Mass Spectrometry, and NMR.

In another embodiment of the invention, a kit containing a bacteria, a group of bacteria, or a bacterial cell culture configured with a reporter gene located within a silent or lowly-expressed gene cluster in the bacteria is disclosed to facilitate the high throughput screenings. This includes application of this approach to any gene cluster in any bacterium, regardless of the source of the bacterium.

One example of such a kit includes a kit targeting the burkholdac (bhc) cluster in E264. Bhc is lowly-expressed under typical growth conditions and produces the histone deacetylase inhibitor. In this case, a kit comprising E264 bacteria having a translational lacZ fusion to bhcF was produced, enabling screenings for bhc production.

Another embodiment of this invention discloses a method of generating a cryptic metabolite. The disclosed method begins by providing a bacterial cell containing at least one gene cluster that is silent or lowly-expressed. Preferably, this gene cluster will consist of a quorum sensing-regulated biosynthetic gene cluster. More preferably, this quorum sensing regulated biosynethic gene cluster will generate a non-cryptic metabolite under normal growth conditions. Once the bacterial cell has been provided, the bacterial cell is exposed to a small molecular modulator, typically previously determined to be an elicitor of a cryptic metabolite. The small molecular modulator may comprise an antibiotic, typically introduced at a quantity below the inhibitor level of that antibiotic. Following standard practices for growing cultures of the particular bacteria provided, a cryptic metabolite may be produced.

As an example, wild type B. thailandensis bacterial cells were first provided. It is well-known that the bta quorum sensing-regulated gene cluster on B. thailandensis normally generates bactobolins. Using the disclosed method, *B. thai-*

*landensis* E264 grown on an LB agar plate was used to inoculate 5 mL of LB medium in a 14 mL sterile culture tube. After overnight growth at 30° C. and 250 rpm, the culture was diluted to an $OD_{600\,nm}$ of 0.05 into 50 mL of LB in a 250 mL Erlenmeyer flask. This culture was grown overnight at 30° C. and 250 rpm and used to inoculate 650 mL LB-Mops (LB+50 mM Mops, pH 7) in each of 12×4 L Erlenmeyer flasks. The initial $OD_{600\,nm}$ of the large cultures was 0.05 and the cultures contained 30 µM trimethoprim (a bacteriostatic antibiotic), prepared as a 10 mM stock in DMSO. After 26 h growth at 30° C. and 200 rpm, the cultures were extracted twice with one volume of ethyl acetate. To verify that the cryptic metabolites had been produced, the organic layers were then combined, dried over $Na_2SO_4$, and evaporated completely in vacuo. The remaining residue was resolved by solid-phase extraction using a 10 g Seppak-C18 column, which had been washed with MeCN and equilibrated with 15% MeCN in $H_2O$. Step-wise elution was performed with 100 mL of 15%, 35%, 55%, 75%, and 100% MeCN (in $H_2O$), all containing 0.1% formic acid. The 55% MeCN fraction contained the previously unknown cryptic metabolites.

These were further purified on a manual Hypercarb column (Fisher Scientific), which had been equilibrated with 20% MeCN in $H_2O$. Step-wise elution was performed with 15 mL of 20%, 35%, 50%, 75%, and 100% MeCN (in $H_2O$+0.1% (v/v) formic acid). The 35% and 50% MeCN fractions were combined, dried in vacuo, resuspended in MeOH, and purified by reverse-phase HPLC on a preparative Eclipse XDB-C8 column (Agilent, 7 µm, 21.2×250 mm) operating at 12 mL/min. The elution program started with an isocratic step (5 min, 20% MeCN in $H_2O$), followed by a gradient from 20-100% MeCN (+0.1% formic acid) over 30 min. The desired cryptic metabolites eluted at ~62-68% MeCN, and fractions containing the cryptic metabolites were combined, dried in vacuo, and further purified by reverse-phase HPLC on a preparative Luna C18 column (Phenomenex, 5 µm, 21.2×250 mm) operating at 12 mL/min. The elution program included an isocratic step (30 min, 30% MeCN in $H_2O$), followed by a gradient from 30-100% MeCN (+0.1% formic acid) over 20 min. The desired cryptic metabolites eluted at approximately 74-80% MeCN. Fractions containing this desired cryptic metabolite were combined and further purified by reverse-phase HPLC on an analytical Synergi Fusion-RP column (Phenomenex, 4 µm, 4.6×250 mm) operating at 1 mL/min. These cryptic metabolites were eluted isocratically at 32% MeCN in $H_2O$ (+0.1% formic acid) over 50 min, and they eluted in separate fractions between 33 and 46 minutes, yielding 0.6-3 mg of pure material.

Disclosed also is the class of materials called acybolins resulting from use of the method described above. This class of materials typically has a molecular formula of:

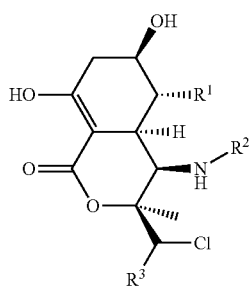

(I)

wherein $R^1$ consists of H or OH, $R^2$ comprises a plurality of amino acids and at least one functional group, and $R^3$ consists of H or Cl. While this invention encompasses a range of amino acids, a preferred embodiment consists solely of alanine, glycine, or both. Further, the functional group is preferably an acyl group, and more preferably an acyl group having a carbon chain of between around 2 to around 20 carbons in length, and more preferably between around 6 to around 12 carbons in length.

As an example, six acybolins were generated using the example method above. In each, the acyl group was 3-hydroxydecanoyl. Those acybolins had structures as follows: Acybolin A was found to have $R^1$=H, $R^2$=Ala-Ala-Ala-Gly-Acyl, and $R^3$=Cl; Acybolin B was found to have $R^1$=OH, $R^2$=Ala-Ala-Ala-Gly-Acyl, and $R^3$=Cl; Acybolin C was found to have $R^1$=H, $R^2$=Ala-Ala-Gly-Ala-Gly-Acyl, and $R^3$=Cl; Acybolin D was found to have $R^1$=H, $R^2$=Gly-Ala-Ala-Gly-Acyl, and $R^3$=Cl; Acybolin E was found to have $R^1$=H, $R^2$=Ala-Ala-Gly-Gly-Acyl, and $R^3$=Cl; and Acybolin F was found to have $R^1$=OH, $R^2$=Ala-Ala-Gly-Acyl, and $R^3$=Cl.

What is claimed is:

1. A molecule of the formula:

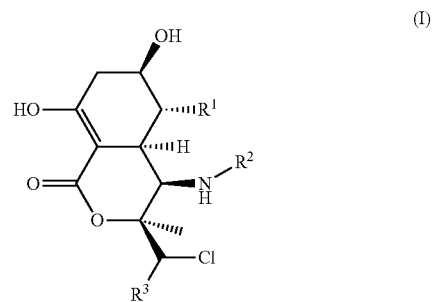

(I)

wherein $R^1$ consists of H or OH, $R^2$ comprises a plurality of amino acids and at least one functional group, and $R^3$ consists of H or Cl, wherein the at least one functional group is an acyl group containing a carbon chain of between around 2 to around 20 carbons in length.

2. The molecule of claim 1, wherein the plurality of amino acids consist of alanine, glycine, or both.

3. The molecule of claim 1, wherein the acyl group contains a carbon chain of between around 6 to around 12 carbons in length.

4. The molecule of claim 1, wherein $R^2$ contains between 4 and 6 amino acids.

* * * * *